United States Patent [19]

Bölsing

[11] 4,350,598

[45] Sep. 21, 1982

[54] PROCESS FOR EVEN DIVISION OF SUBSTANCES AND MIXTURES OF SUBSTANCES IN THE COURSE OF MANUFACTURING OF PULVERULENT PREPARATIONS BY CHEMICAL REACTION

[76] Inventor: Friedrich Bölsing, Danziger Str. 5, D-4965-Lindhorst, Fed. Rep. of Germany

[21] Appl. No.: 111,977

[22] Filed: Jan. 15, 1980

Related U.S. Application Data

[63] Continuation of Ser. No. 709,385, Jul. 28, 1976.

[30] Foreign Application Priority Data

Jul. 29, 1975 [DE] Fed. Rep. of Germany ....... 2533789

[51] Int. Cl.$^3$ ............................................. C02C 5/02
[52] U.S. Cl. .................................. 210/751; 210/766; 423/DIG. 15; 423/630; 423/659; 71/64.1; 208/13
[58] Field of Search ....................... 423/DIG. 15, 640; 208/283; 210/751, 766

[56] References Cited

U.S. PATENT DOCUMENTS

| 1,195,140 | 8/1916 | Keck | 423/640 |
|---|---|---|---|
| 1,348,494 | 8/1920 | Horn | 423/640 |
| 2,053,209 | 9/1936 | Snow | 208/283 |
| 2,497,636 | 2/1950 | Stowell | 423/640 |
| 3,897,238 | 7/1975 | Bolsing et al. | |
| 4,028,240 | 6/1977 | Manchak . | |
| 4,079,003 | 3/1978 | Manchak . | |

FOREIGN PATENT DOCUMENTS 2614848 10/1977 Fed. Rep. of Germany ...... 210/751

OTHER PUBLICATIONS

Bolsing et al., "Zement-Kalk Gips", vol. 25, 1972, #5, pp. 254–257. (Translation pp. 1–20).

Primary Examiner—Herbert T. Carter

[57] ABSTRACT

A process for forming uniform distributions of at least one substance in a solid. The process comprises forming a predistribution of the at least one substance in at least one compound, e.g., mixing the at least one substance so that it is distributed throughout the at least one compound, and reacting the at least one compound with water to form a hydroxide, which hydroxide has a larger surface area than the at least one compound. Predistribution must take place before a substantial portion of the compound reacts to form the hydroxide. This process can be used to form a dry powder having at least one substance uniformly distributed therein.

7 Claims, No Drawings

PROCESS FOR EVEN DIVISION OF SUBSTANCES AND MIXTURES OF SUBSTANCES IN THE COURSE OF MANUFACTURING OF PULVERULENT PREPARATIONS BY CHEMICAL REACTION

This is a continuation of application Ser. No. 709,385 filed July 28, 1976.

The present invention relates to a process for even division, i.e., the uniform distribution or dispersion of a substance or a mixture of substances in the course of manufacture of pulverulent preparations by means of chemical reaction.

Chemical substances are generally divided mechanically in the course of manufacture of pulverulent preparations, e.g. by grinding processes. There are often substantial disadvantages inherent in the mechanical methods. Thus, for example it is often difficult or impossible to distribute uniformly substances that are oily or pasty, adhering or sticky, on a finely granular support material, to produce a dust-dry pulverulent homogeneous preparation.

Either the quantity of such material that is to be divided is too small to permit a uniform distribution in all particles of the pulverulent preparation, or it is too large, so that whereas all particles are coated there is also a free unbound phase, i.e., a surplus, that bonds the particles and thus prevents the production of a dust-dry pulverulent preparation.

Thinly fluid materials and mixtures, especially solvent-containing materials such as aqueous solutions, emulsions and suspensions, are difficult to divide mechanically, insofar as they require a large quantity of finely granular adsorptive material to produce a pulverulent dust-dry preparation.

In addition to the mechanical process, there are chemical methods for distribution of substances and mixtures of substances, to form pulverulent preparations.

Thus, it is possible to distribute mineral oils or oils of other origin, bituminous materials or waxes or the like, by mixing them with a compound that forms a hydroxide with water, and converting this compound to the hydroxide with a stoichiometrically equivalent amount of water.

Further, it is possible to distribute waste materials in a solid by mixing them with an alkaline earth oxide which is pretreated with boundary-layer surfactants that delay the reaction with water, and allowing the alkaline earth oxide charged with the waste materials to react with about a stoichiometrically equivalent amount of water, to form alkaline earth hydroxide.

Although the chemical processes constitute considerable advance over mechanical processes, there are certain drawbacks associated with chemical processes.

According to the one chemical process, no aqueous materials and mixtures may be reacted; it is limited to substantially anhydrous mineral oils or oils of other origin, as well as to substantially anhydrous bituminous materials or waxes and the like. The necessary reaction water may only be introduced after the substance that is to be distributed has been introduced.

According to a second chemical method, an alkaline earth oxide must be used that is pretreated with boundary-layer surfactants.

The present invention is addressed to the problem of creating a process whereby substances and mixtures of substances, especially oily or pasty, adhering or sticky materials as well as thinly liquid substances and mixtures, especially those that contain a solvent, such as aqueous solutions, emulsions and suspensions, may be simply, evenly and optimally distributed to form pulverulent preparations.

The subject of the invention is a process for uniform distribution or dispersion of a substance or a mixture of substances in the course of the manufacture of pulverulent preparations by a chemical reaction, characterized in that a substance or a mixture of substances, in a state suitable for predistribution are brought so rapidly to uniform comprehensive predistribution in a compound that forms a hydroxide with water that the rate of this predistribution is higher than the rate of reaction of the compound that forms a hydroxide with the water. The compound that forms a hydroxide with water, after take-up of the substance or mixture of substances that effects the predistribution of the said substances that are to be distributed by a chemical process, is reacted with water to form a hydroxide.

Accordingly, the subject of the invention is a process for the uniform distribution of a substance or a mixture of substances in the course of the manufacture of pulverulent preparations by chemical reaction that is characterized in that the substance or mixture of substances in a state suitable for a predistribution in a compound that forms a hydroxide with water are brought so rapidly to a uniform comprehensive predistribution that the rate of predistribution is higher than the rate of reaction of the compound that forms a hydroxide with water, and the homogenized product that is not yet in reaction is allowed to react outside the zone of mechanical homogenizing, to form a pulverulent homogeneous preparation.

The substance or mixture of substances in a state suitable for a preliminary distribution are those especially in a fluid state, namely a substance in a liquid state without solvent or as a fluid preparation, such as a solution, emulsion, suspension or in a solid preliminarily divided state, whether or not the said substance or mixture be oily, pasty, adhering or sticky, or especially thinly liquid, and whether or not the said substance or mixture of substances contain water. Insofar as the substance or mixture of substances contain no water, or insufficient water for the chemical reaction of a compound that forms a hydroxide with water, there is simultaneous addition of water as such or in the form of an aqueous preparation.

Since in the framework of the present invention, what is involved are substances and mixtures of substances, this term is to be understood in its broadest sense. Organic and inorganic substances and mixtures may be considered insofar as they are capable of predistribution according to the present invention.

The applicability of the process of the present invention is largely independent of the physical state of the substances and mixtures of substances. It is possible to conduct the process, for instance, if there are organic materials present at low temperature as solids suspended in water, for example, which only become liquid with elevation of the temperature or under the effect of a solvent. The process can relate not only to a single-phase system or two-phase systems comprising water and an organic liquid that is immiscible or only miscible with water to a limited extent, but also to multiphase systems that include ultrafinely divided solids. Also, the viscosity of the substances and mixtures of substances plays no decisive part as to the applicability of the process.

The applicability of the process of the present invention is also largely independent of the chemical nature of the substances or mixtures of substances. The substances concerned can be monomeric compounds as well as polycondensates or polyaddition compounds. These substances may be of natural or synthetic origin. For example, mineral oils and mineral oil products such as oil from salvage products, vegetable and animal oils (fats), waxes and waxlike products, tar oils, resins and resin-like substances (synthetic resins), bituminous substances, pitches, acid sludge, oridinary hydrocarbons and functional derivatives. The foregoing materials may be present as solutions, emulsions and suspensions. The solutions may contain water or organic solvents. This applies similarly for emulsions and suspensions. Examples of solutions, emulsions and suspensions are metallic salt solutions, synthetic resin emulsions, oil emulsions, galvanic sludges, red muds, settling slurries, waterglass solutions, pasty silicic acid, waste from battery raising of animals (liquid manures). Also applicable are fullers' earth loaded with oils or other oil-like materials, multi-phase systems such as oil-and-water mixtures, and gels such as solvent-containing wastes of chemical materials.

It is also of no importance, if the material is capable of being distributed as such, or if it has to be pretreated, e.g. by dilution with solvent or after a preliminary chemical neutralization. Substances and mixtures of substances, which themselves react chemically or which can react with the components of the auxiliary reaction involving the formation of the hydroxide, can be combined to make use of their enhanced chemical reactivity in the ultrafinely divided form, e.g. in the division of pasty silicic acid or fullers' earths, with use of calcium oxide.

For execution of the inventive process, suitable are chemical compounds that can be converted in a chemical reaction in such a way that a new material is produced which has a larger surface area than that of the starting material. This applies to reactions in which hydroxides are produced by reaction with water. All alkaline earth oxides are especially suitable for this, i.e. the oxides of calcium, barium, strontium or magnesium. For the purposes of the invention, calcium oxide is preferred, in the form of commercial burned lime, for example "white lime," but coarse granules are usable in many instances.

Because of the preferred use of burned lime, the following processes and advantages of the invention are described only with reference to calcium oxide, although they apply essentially, as well to the other alkaline earth oxides or mixtures thereof. Moreover, specific alcoholates such as aluminum alcoholates are suitable, especially aluminum alcoholates that are liquid at ambient temperature. Additionally, two or more compounds that form a hydroxide with water may be used together. The basic concept of the invention will be indicated using the example of an aluminum alcoholate.

The distribution of a substance or mixture of substances by chemical reaction according to the invention has the following concept as its basis.

If a material A reacts with a material B in such a way that a material C results which has a larger internal and external area than A or B, then materials D, E, etc. can be distributed by chemical methods provided that they can be homogeneously predistributed in A or B before commencement of the reaction of A with B. The reaction $A+B \rightarrow C$, underlying the distribution and designated the auxiliary reaction, accomplishes the distribution of D, E etc.; the materials that are to be distributed are themselves, in general, not subject to any chemical interaction with A, B and C.

The hydrolysis of aluminum alcoholates to aluminum hydroxide and alcohol may serve as a model reaction, which provides an especially significant increase of the surface area of one of the starting materials.

To illustrate the basic idea advantageous use is made of Al sec. butanolate which is liquid at room temperature and which is decomposed under the action of atmosphere moisture to a finely granular aluminum hydroxide and evaporating alcohol. The compound that is produced in the auxiliary reaction, in contrast to the starting material, has a surface area enlarged by several powers of 10.

A substance that is homogeneously predistributed in the coherent phase of the unreacted liquid alcoholate for example, a dissolved material such as a liquid dye, is so transferred into the newly produced structure of the reaction product that each individual aluminum hydroxide particle mainly contains dye fractions.

A liquid dye may now not only be present dissolved in the aluminum alcoholate, but via saturation it may also be present as a separate external phase in addition to the alcoholate.

After completion of the auxiliary reaction, insofar as the amount of the external phase is kept within specific limits, there is also surprisingly present a dust-dry aluminum hydroxide that not only encloses the dye, but also contains the dye adsorbed on its inner and outer surfaces. On the other hand, when the same amount of aluminum hydroxide prepared according to the same basic reaction yet without addition of dye yields with the same quantity of subsequently added dye, only a semi-liquid suspension, it is demonstrated that the adsorption capacity of the new surface formed inside the dye phase is considerably increased apparently because of the exclusion of disturbing foreign adsorption.

A similar situation obtains for the auxiliary reaction with calcium oxide. In line with the behavior of the aluminum alcoholate, it is possible to effect a distribution both without an external liquid phase as well as in the interior of a liquid phase. If, for example paraffin oil is caused to be taken up to the point of saturation in the calcium oxide, where it is not important if the oxide is ground or in large pieces, the conversion with the subsequently calculated amount of water, results in production of a pulverulent calcium hydroxide the individual particles of which contain fractions of paraffin oil.

If, conversely, calcium oxide is charged into paraffin oil beyond the point of saturation, in the course of the reaction with the calculated quantity of water added to the liquid suspension of calcium oxide in paraffin oil there is produced from the suspension, which is further liquified by the water addition, a dust dry powder the individual particles of which are coated uniformly with paraffin oil. A difference with respect to the aluminum alcoholate example, to which difference attention is expressly drawn is that the material to be distributed in the starting calcium oxide need not be dissolved in the true meaning of the term. The preliminary distribution required by the process of the invention is also ensured by the uniform penetration of the oil into all CaO particles.

With reference to the described examples, it is clear that an optimum preliminary distribution, of the substances that are to be distributed, in the interior of the starting material of the auxiliary reaction in question is characteristic of a distribution through chemical reaction. Accordingly "distributions" of those materials that cannot be introduced into the internal structures of the starting materials before the start of the chemical auxiliary reaction cannot be classed among the distributions by chemical reaction according to the present invention process.

If for example metal particles, such as finely pulverized copper, are placed in liquid aluminum alcoholate, the metal can only be suspended in the liquid phase: there is no further interaction. After completion of the auxiliary reaction, i.e. after addition of the calculated amount of water, the formed aluminum hydroxide is present with the unchanged metal particles. None of the individual hydroxide particles contain metal fractions, and the metal is not adsorptively bound. The metallic copper is not capable of preliminary distribution, and therefore it is not distributable by the present process of the invention.

The same consideration applies to the predistribution in calcium oxide. Here also a metal powder cannot be introduced into a starting material of the auxiliary reaction, so that after completion of the chemical reaction, it remains unchanged and is present in addition to the calcium hydroxide. But even in cases in which, in principle, there might be the possibility of a distribution by chemical reaction, there would be no distribution by chemical reaction in the above-mentioned meaning of the term. Thus it is said erroneously that there is distribution if, for example, an oily material is charged into calcium oxide without all the calcium oxide particles being able uniformly to take up, i.e., absorb the oily material, i.e., without optimum preliminary distribution. After completion of the chemical reaction of calcium oxide with water, there are oil-containing calcium hydroxide particles in addition to oil-free calcium hydroxide particles, just as in the case of the metal particles in the previous example.

In order to obtain a true distribution by chemical reaction in the selected example, if the amount of oil-containing substance is relatively small the latter would have to be dissolved in an inert solvent in such a quantity that the solution would reach all the calcium oxide particles. After completion of the reaction, all the calcium hydroxide particles would be charged with the oily material in this way.

Water-soluble substances are dissolved in water in a stoichiometrically equivalent amount with reference to the reaction. Since distribution and adsorption occur in the conversion of calcium oxide to calcium hydroxide, a preliminary distribution in the mentioned sense is not present, but rather a process that serves to predistribute water-soluble substances in the starting component, calcium oxide. If for example metal hydroxides or metal oxides are to be distributed, a suitable salt is dissolved in the calculated amount of water. Here, as in many other cases, it is to be observed that the solvent would react immediately upon addition to the calcium oxide, i.e. before conclusion of the necessary predistribution. Irrespective of predistribution whether the calcium oxide is added to the water or vice versa, before a homogeneous suspension can form the conversion of the oxide to the hydroxide will have already occurred. This process corresponds to that of the incomplete predistribution of a liquid substance.

On the whole, we have the following picture:

For distribution of substances and mixtures of substances by chemical reaction, predistribution is of decisive importance. Untreated calcium oxide reacts immediately with water in a mixture of water and a material that is to be distributed, i.e. before the material to be distributed can be taken up, i.e. absorbed, by the calcium oxide; in other words, before it can be predistributed. A division by chemical reaction according to our process does not occur.

Of course, in such cases a preliminary distribution can be managed if the reaction of the calcium oxide with water is delayed, e.g. by surfactants in the broadest meaning of the term. The sole feature which is decisive here is that the reaction of the calcium oxide with water be delayed at least until the substance to be distributed has been taken up, i.e., is absorbed, completely by the calcium oxide.

The condition of delaying the reaction of calcium oxide with water is eliminated if the material to be distributed is practically anhydrous since it can be predistributed without reaction in the calcium oxide. After this first step however, there then has to be addition of water in a second step, i.e. after the predistribution.

It has been found, surprisingly, that a uniform predistribution of the material that is to be distributed can be attained without a two-stage process and without delay of the reaction of the calcium oxide, in a single work step, and in the presence of water.

Thus water-containing substances, e.g. aqueous solutions such as metal salt solutions; aqueous emulsions and suspensions, can be converted with untreated calcium oxide to a powdery calcium hydroxide product in which the substance and the water, to the extent that it is not chemically consumed or evaporated in the exothermic reaction, are most finely divided with exploitation of the maximum adsorption capability as a consequence of a thorough predistribution. Anhydrous materials can be converted to a pulverulent final product with avoidance of a two-stage process directly with the necessary reaction water and calcium oxide, the material in the final product being ultrafinely divided. In any case, the water necessary for the reaction can be supplied in the form of aqueous preparations, e.g. as aqueous solutions or emulsions, or added supplementarily. In this way, the content of the aqueous preparations is ultrafinely divided. Also very large surpluses of water, as they exist in many slurries, often more than 90%, have no disturbing effect. Either materials that impart a hydrophobic effect are distributed, simultaneously and thereby producing hydrophobic dusts from which the excess water spontaneously separates, or practically speaking, the water that is not consumed in the chemical auxiliary reaction and the water that is not vaporized in the exothermic reaction in the sense of the invention, is added in similar form, i.e., distributed in the dust that is produced, which dust as a consequence of the substantially enhanced adsorption capability in terms of the invention, takes up surprisingly large quantities of water without losing its powdery consistency. This water-binding effect can be still further increased, e.g., in the distribution of settling slurries, if at the same time other water-binding swellable materials are also divided, e.g. peat dust, bentonite, swellable macromolecular substances etc.

Mechanical mixers are used for execution of the process of the invention, which ensure that the rate of predistribution will be higher than the rate of reaction with water of the compound that forms a hydroxide with water.

Thus for example a gravity tube only a few centimeters high may be used, wherein beaters, paddles or other agitating vanes turn at high speed about a shaft, for example at more than 1500 rpm. The materials that are to undergo predistribution fall separately in the tube, are there often homogeneously mixed in less than a second, and leave the tube without any appreciable reaction, generally in the liquid state. The distributing auxiliary reaction only begins outside the pipe, and the pulverulent preparation with optimally distributed materials is produced according to the invention.

This predistribution may also be effected in an apparatus with a horizontal shaft. Here the homogenized material also leaves the mixing device in less than a second, through a tangential discharge passage. Fast-running so called thin film mixers are also usable if the residence time of the homogenized material is kept very brief. In this case, the chemical process sets no special requirements on the mixer. It must only be ensured that the starting components to be homogenized be mixed homogeneously at a speed that is higher than the rate of reaction observable in the case in question.

As comparative experiments have shown, the invention can be described in its chemical aspect as follows. The chemical reaction of the calcium oxide with water occurs in an exothermal reaction. The progress of the reaction can be followed in a temperature diagram. Here it is seen that the reaction temperature rises extraordinarily vigorously in the first minutes of the total reaction time, and the reaction thus progresses very rapidly, with formation of calcium hydroxide that is not usable for a distribution by chemical reaction. If the reaction of the calcium oxide is delayed, e.g. with agents that promote hydrophobic properties, the rise of the reaction temperature is delayed, as far as time is concerned, and is slower as far as the temperature rise is concerned. Time has now been gained, before any notable reaction of the calcium oxide with water, to effect a predistribution of the material to be divided, in calcium oxide that is not affected by the water. The basic concept of the invention, even with rapidly rising reaction temperature, thus at a rapid chemical reaction of the calcium oxide with water, is to effect nonetheless a predistribution of the material to be distributed in calcium oxide not influenced by the water, so that this predistribution occurs very fast, i.e. before a few seconds have elapsed, for example, that are required for an observable reaction of the calcium oxide with water. In cases in which the water contains components such as acids that initiate the reaction more rapidly than usual, the time span available for a predistribution is even shorter, for example, fractions of a second. On the other hand, the substances to be distributed or the water, or the water-containing material may contain compounds that act on their own to delay the reaction in comparison to the usual reaction. Here, as a result, the time available for the predistribution may often be extended to minutes.

EXAMPLES (1*a*) 56 kg calcium oxide are homogenized with 25 kg of an aqueous copper sulfate solution (10%) in a fast-running gravity tube mixer. The homogenized material leaves the mixer in a thinly liquid form. In the auxiliary reaction that immediately starts, the copper salt is homogeneously distributed. In secondary reactions, copper hydroxide is produced from the ultrafinely divided copper salt, and with simultaneous distribution of reducing agents, ultrafinely divided metallic copper. The material is a basic catalyst. The actual catalysts, i.e. the metal salts or subsequent products, are so extremely finely divided and chemically so active that, in contrast to all ordinary processes, it is no longer necessary to undertake a supplementary activation.

(1*b*) Stoichiometric amounts of aluminum-secondary butanolate, water and copper salt are homogenized and reacted as described above. The alcohol produced in the hydrolysis is evaporated. An acid catalyst is produced.

(1*c*) A concentrated copper salt solution, calcium oxide and aqueous pasty silicic acid are quantitatively homogenized and brought to reaction resulting in production of a dust-dry finely granular neutral copper catalyst.

(1*d*) In consideration of the water content of a pasty silicic acid, stoichiometric quantities of aluminum-secondary butanolate and a concentrated aqueous copper salt solution are homogenized. An aluminum copper catalyst is produced.

The copper content of the aqueous solution can be increased by preparing with addition of ammonia, a tetramine complex.

All the catalysts thus produced via a distribution by chemical reaction have such high activity that entirely novel types of reactions, particularly in the field of organic chemistry, can be effected with them. The same is true for other metal salts. Especially, catalysts with use of noble metals can be prepared more economically, because by virtue of the increased activity, lesser amounts of noble metals are required with equal activity of the catalysts.

The above examples are significant to the extent that they show the importance of the concept of complete uniform distribution in all calcium oxide particles. If we leave this criterion aside, that the rate of predistribution has to be higher than the rate of reaction of the auxiliary reaction, and mix the components together without consideration of this compelling necessity, then with immediate initiation of the auxiliary reaction a precipitation of metal compounds with shell-like clumping occurs, with high concentrations of metal compounds, whereas other zones remain practically devoid of metal. Even if there is a subsequent mechanical pulverizing of the reacted mixture, to a considerable extent not all particles are coated with the catalytically active metal derivatives. This deficient distribution, which is not encountered according to the process of the invention, shows impressively that these systems have practically no catalytic effect.

(2) 56 kg calcium oxide, 28 kg flowers of sulfur and 20 g water are homogenized in a gravity tube mixer, whereby after a few seconds the chemical auxiliary reaction sets in outside the mixing device. Here a yellow powder is first produced, with homogeneously distributed sulfur. The distributed is so extreme that after a short time secondary reactions occur in the dust-dry power. WIth brown coloration, sulfides are formed, and thereafter sulfur is separated out, whereby hydrogen sulfide goes off in large quantities. The separated molten sulfur begins to burn spontaneously.

(3*a*) Chemical compounds that basically would be capable of a chemical reaction that does not occur under ordinary conditions, however, and that can only be brought to reaction with difficulty under drastic conditions, can be caused to react in a simple way if they are reacted in the course of the described exothermal distribution reaction according to the present invention. This is to be attributed to the fact that the chemical reactivity increases with the degree of distribution. The example under (2) belongs in this category also, because in one step sulfides can be prepared from calcium oxide, sulfur and water, to the extent that the reaction is held at this stage by cooling.

(3b) 1.72 kg benzophenone dissolved in an inert organic solvent, 2.8 kg calcium oxide, 0.6 kg of an aqueous hydrazine solution and 0.6 kg water are homogenized according to the process of the invention. After completion of the auxiliary reaction, the produced powder is extracted with an organic solvent, to recover the benzophenone hydrazone that was produced. For comparison: according to the known directions, the benzophenone hydrazone is obtained by 8 hours of heating at 150°–200° C. with anhydrous hydrazine in the autoclave.

(3c) Reaction (3b) can be conducted with use of an aluminum alcoholate.

(4) A solution of bentazone, a herbicide, is homogenized with stoichiometric quantities of calcium oxide and water. After completion of the auxiliary reaction, the herbicide is optimally distributed in the produced calcium hydroxide. The powder may be added to fertilizers for rice plantations. If there is to be a prevention of [flying] dust in direct application of the herbicide-containing powder, a dust-binding agent such as paraffin oil is added. If the material is to be utilized in a hydrophobic state, an agent such as fatty acid is added. It is an advantage of the inventive process that one is able in the simplest way, by distribution by means of chemical reactions, to use any number of materials in optimal distribution.

(5) 50 t oil from salvage products is homogenized with 50 t calcium oxide and 20 t water. A dust-dry powder is produced which, for example, may be used for building up base layers, or as a bituminous filler.

(6) 50 t oil slurry (50% water) is homogenized with 30 t calcium oxide. A dust-dry powder is produced which, as described under (5) can be put to use.

(7) 56 t oil from salvage products with 56 t calcium oxide and 56 kg red slurry, i.e., a conversion residue of bauxite during the manufacture of aluminum also known as red mud, are homogenized in a thin film mixer. After the chemical reaction, there is produced a brownish red, dust-dry powder that can be used as a bituminous filler, for example.

(8) 56 kg calcium oxide and 100 kg pasty silicic acid are homogenized. Calcium silicates are produced that can be used, for example, in the building materials industry. The product under (8) may be mixed with 90 kg oil from salvage products or acid sludge. Dust-dry powders are produced.

(9) 100 kg of a waste material from a poultry farm (liquid manure) is homogenized with 30 kg calcium oxide. A dusty-dry powder is produced wherein the organic substance of the waste material is homogeneously distributed. It can be seen from this example that just the predistribution according to the present invention yields optimal results. It is known that calcium oxide can be used to remove water from water-containing slurries. Here the calcium oxide is added to the water-containing slurry in such a way that the reaction with the water begins before the aqueous slurry has been homogeneously predistributed. Thus it is true that the stoichiometric amount of water is consumed, and also that part of the water evaporates through the exothermal reaction, but the surplus water remains in the produced crumbly, essentially unhomogeneous mass. Only by the predistribution of the water-containing slurry according to the present inventive process can the optimal adsorption capability that comes into effect, of the newly-produced surfaces, optimally adsorb water in the vicinity because there are no disturbing foreign adsorptions, as we have already noted. Thus with little calcium oxide, a homogeneous dry powder is obtained that contains a major part of the water bound by uniform adsorption.

Fertilizing agents may be divided, along with the product. If these agents are readily soluble in water, then the co-distribution according to the invention is effected without any other measures. If they are sparingly soluble, they are treated in a pre-mixer with the liquid manure until there is optimal predistribution, and only thereafter are the reacted according to the invention.

Thus are formed fertilizer-like preparations. With use of peat dust and the like, valuable soil-improving agents are obtained.

(10) Similar conditions as in example (9) apply for the reaction of settling slurries, i.e., sewage sludges, which may contain as much as 95% water. A large amount of water can only be uniformly bound if an optimal predistribution has been effected in a fast running homogenizer. Several cubic meters of a settling slurry from a biological settling station were reacted in a gravity tube mixer with throughput of 2 m$^3$/hour with simultaneous addition of calcium oxide. The homogenized product left the mixing device as a thinly liquid slurry. After completion of the chemical reaction in a collecting receptacle there was produced a uniform powdered product that can be used as a so-called lime fertilizer. Other water-binding or gell substances may also be added, e.g. used fullers' earth (also as soil improving agent or for production of recultivating agents) and/or organic water-binding components, for example, so called swelling agents. Additionally fertilizing components may be added to the above identified product, e.g., potassium salts, nitrates, phosphates, as well as trace element compounds, before the predistribution, and distributed along with the product in order to increase the fertilizing value.

(11) 5.6 kg of fresh acid sludge, i.e., an acid resin, is homogenized with the same quantity of a red slurry, a pasty silicic acid or the like, or with half the amount of a heavily watered slurry, or with half the amount of water and 5.6 kg calcium oxide. A sulfate-containing, dust-dry, finely granular powder is produced, that can be utilized industrially in other operations. This reaction can be so conducted, by changing the quantitative relationships, that with mixing of the acid sludge and the calcium oxide, there is a vigorous reaction immediately after leaving the mixing device (residence time in this case should be only fractions of a second) whereby such large amounts of sulfur dioxide are expelled that this device can be used as a sulfur dioxide generator. For this purpose, the reaction is allowed to proceed in a closed system from which the released sulfur dioxide is removed by suction and prepared for further use. Depending upon the intensity of the eduction flows, the sulfur dioxide flow can be controlled. The residue formed in the chemical auxiliary reaction is again a dry powder, this time however practically devoid of sulfate, so that here other possibilities for further use are included. A reaction of acid sludge without release of sulfur dioxide is analogously successful, through addition especially of organic components such as oils and oil-like substances, solvents, solvent-containing resin dispersions and the like.

(12) Also oils that are in the ground or water can be reacted according to the invention. Because the soil generally is moist it suffices to treat the oil-charged soil in a fast running mixer with calcium oxide. Additionally, in the second case, water is present so hat only calcium oxide has to be added. After leaving the mixing device, the auxiliary reaction is completed and from the oils there are produced dust-dry powders, or depending upon the kind of oil, ultra-finely divided suspensions in water. If the water is to be separated from the oil, there is simultaneous distribution of an agent that imparts hydrophobic properties, to the extent that the oil itself does not naturally have such properties. There are thus produced dust-dry hydrophobic powders that separate spontaneously from the surplus water.

(13) Paint residues, slurries and plastics dispersions, e.g. waste from coating facilities and spray-paint stalls, which as a rule contain substantial amounts of solvent, e.g. acetic acid ethyl ester and cyclohexanone, are homogenized and reacted, with addition of equal amounts of calcium oxide and half the amount of water. Powder or granulates are produced which in many situations can be further utilized, e.g. as oil absorbents. The necessary reaction water can again be supplied in the form of aqueous slurries, e.g. galvanic slurries. If the plastic concerned is a thermoplastic, the ultrafinely divided galvanic slurries can be embedded in the plastic by a subsequent treatment, e.g. by compression in a heatable press.

I claim:

1. A process for forming a uniform distribution of an oil in calcium hydroxide comprising:

A. adding calcium oxide to an oil which is in the presence of water, and
   B. mechanically mixing said oil with said calcium oxide, said calcium oxide being capable of reacting with said water to form calcium hydroxide which has a surface area greater than the surface area of said calcium oxide, said mechanical mixing homogenizing said calcium oxide, water and oil so that said oil is substantially homogeneously distributed within said calcium oxide prior to the observation of the temperature increase associated with the exothermic reaction between calcium oxide and water, wherein said mechanical mixing substantially homogeneously distributes said substance within said hydroxide forming compound at a rate faster than the rate of reaction between water and said hydroxide forming compound, said mixing step being performed in the absence of compounds which delay the reaction between calcium oxide and water, and upon the reaction between said calcium oxide and water to provide said calcium hydroxide, a dust-dry substantially uniform distribution of said oil in calcium hydroxide is provided.

2. The method according to claim 1 wherein said oil is a mineral oil.

3. The method according to claim 1 wherein said oil in the presence of water comprises oil in moist soil.

4. The method according to claim 1 wherein said oil in the presence of water comprises a slurry of oil in water.

5. The method according to claim 1 wherein said oil is selected from the group consisting of vegetable and animal oils, salvage oil, tar oils and paraffin oil.

6. The method according to claim 1 wherein said calcium oxide is in the form of white lime.

7. The method according to claim 1 wherein said mixing is carried out in a thin film or gravity tube mixer.

* * * * *